United States Patent [19]

Plattner et al.

[11] 4,371,546

[45] Feb. 1, 1983

[54] BENZOPHENONE DERIVATIVES

[75] Inventors: Jacob J. Plattner, Libertyville; Andre G. Pernet, Evanston; Anthony K. Fung, Waukegan, all of Ill.

[73] Assignee: Abbott Laboratories, North Chicago, Ill.

[21] Appl. No.: 310,165

[22] Filed: Oct. 9, 1981

[51] Int. Cl.³ .................... A61K 31/135; C07C 97/10
[52] U.S. Cl. .................... 424/330; 564/323; 564/324; 564/328
[58] Field of Search .................. 564/323, 324, 328; 424/330

[56] References Cited

U.S. PATENT DOCUMENTS 3,123,643  3/1964  Palopoli et al. .................. 564/323
3,285,912  11/1966  Palopoli et al. .................. 564/323
3,560,567  2/1971  Ruegg et al. ..................... 564/324

*Primary Examiner*—Johnnie R. Brown
*Assistant Examiner*—Frederick W. Pepper

*Attorney, Agent, or Firm*—Gildo E. Fato; Robert L. Niblack

[57] ABSTRACT

Described are compounds of the formula

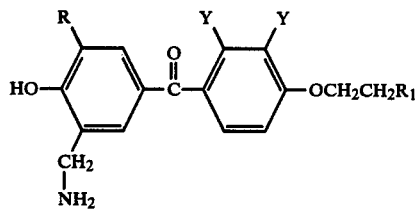

wherein R is hydrogen, loweralkyl, aminomethyl or halo, $R_1$ is hydroxy or NHX where X is H, loweralkyl, phenyl, substituted phenyl, acetyl, benzyl and substituted benzyl, and Y is hydrogen, loweralkyl or halo and may be the same or different, and pharmaceutically acceptable salts thereof.

The compounds are effective as diuretic agents.

15 Claims, No Drawings

BENZOPHENONE DERIVATIVES

BACKGROUND OF THE INVENTION

The present invention provides compositions for the treatment of hypertension, edema, cadiac failure, and other conditions involving fluid and electrolyte accumulation. A diuretic composition in dosage unit form is described.

SUMMARY OF THE INVENTION

The present invention is directed to compounds of the formula

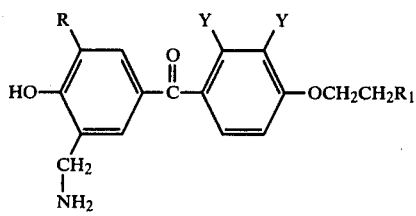

wherein R is hydrogen, loweralkyl, aminomethyl or halo, $R_1$ is hydroxy or NHX where X is H, loweralkyl, phenyl, substituted phenyl, acetyl, benzyl and substituted benzyl, and Y is hydrogen, loweralkyl or halo and may be the same or different, and pharmaceutically acceptable salts thereof.

The term "loweralkyl" as used herein refers to straight or branched chain alkyl radicals containing from 1 to 6 carbon atoms including but not limited to methyl, ethyl, n-propyl, iso-propyl, n-butyl, sec-butyl, 2-methylhexyl, n-pentyl, 1-methylbutyl, 2,2-dimethylbutyl, 2-methylpentyl, 2,2-dimethylpropyl, n-hexyl and the like.

The term "halo" as used herein refers to chloro, bromo, fluoro and iodo.

The term "pharmaceutically acceptable salts" includes nontoxic acid addition salts of the compounds of the invention which are generally prepared by reacting the free base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate, and like salts. Also included are metallic salts such as the sodium or potassium salt of the acid.

The present compounds may be administered to warm-blooded animals orally or parenterally. They can generally be administered with a pharmaceutical carrier. The term "pharmaceutical carrier," for the purpose of the present invention, is intended to refer to any medium that is suitable for the preparation of a dosage unit form, and thus includes the tablet medium or a pharmaceutically acceptable vehicle or solvent such as is ordinarily used in the preparation of intravenous or intramuscular solutions.

A pharmaceutical composition containing the compound can be administered to warm-blooded animals in parenteral or oral dosage form. For oral administration, amounts of from about 0.1 to 200 mg./kg. per day per patient are useful, with the total dose of up to 1 gm. per day being a suitable range for large animals, including humans. The whole dosage range described increases the total urinary excretion from about 2 to about 10-fold in most animals. From these figures, it is apparent that the new diuretic compounds are particularly effective in increasing urinary excretion in most animals.

For all dosage forms, the above exemplified compounds can be placed in capsules, formulated into pills, wafers or tablets in conventional fashion together with pharmaceutical carriers well known in the art. Tablets may be prepared for immediate release of the active compound or they may be made enteric, i.e., whereby the active ingredient is released slowly over a period of several hours from within the intestinal tract.

DETAILED DESCRIPTION OF THE INVENTION

In order to illustrate the manner in which the above compounds may be prepared and the properties of the compounds, reference is made to the following examples, which, however, are not meant to limit or restrict the scope of the invention in any respect.

The phenoxyethanol derivatives of the invention were prepared according to the following reaction scheme. Compounds of the invention other than depicted can be made in the same manner using the appropriate starting materials.

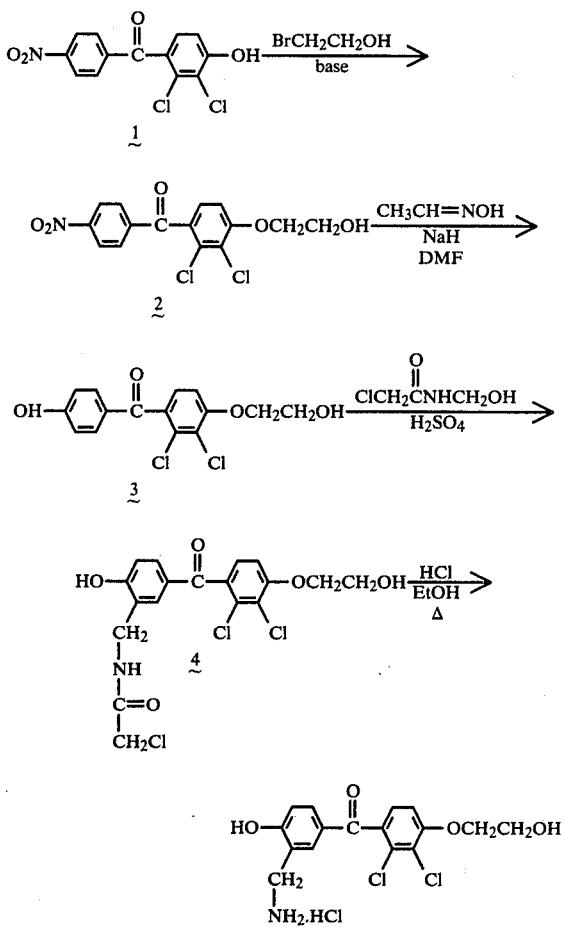

Alkylation of the phenol (1) with bromoethanol in dimethylformamide (DMF) gave the ether (2). Replacement of the nitro group by hydroxyl was effected by acetaldoxime/NaH in dimethylformamide solution. The resulting phenol (3) was coverted to the desired final product (5) by amidoalkylation and hydrolysis of the chloroacetyl group.

The phenoxyethylamines described in this invention were prepared in the following manner. The amine function in compound (5) was protected as the carbobenzoxy (CBZ) derivative. The ester function was then converted to carboxamide with ethanolic ammonia. Dehydration of the amide with trifluoroacetic anhydride in pyridine led to the nitrile which was converted to the desired bis-amine by hydrogenation over palladium or charcoal.

EXAMPLE 1

2,3-Dichloro-4-(4'-nitrobenzoyl)phenoxyethanol 2,3-Dichloro-4-(4'-nitrobenzoyl)phenol (93 g., 0.298 mole) was dissolved in 300 ml. dry DMF, and was filtered into a one liter flask. Powdered potassium carbonate (19.07 g., 0.298 mole) was added in one portion. The suspended mixture was stirred at 80° C. for 1½ hours and was treated by dropwise addition with freshly distilled 2-bromoethanol (37.25 g., 0.298 mole). After the addition was completed, the reaction mixture was stirred at 80°–85° C. for 16 hours.

The mixture was poured into 2 l of $H_2O$ and filtered. The filtered residue was washed well with 1% NaOH, (from the NaOH solution was recovered 20 g. of starting material) and then with $H_2O$. Finally, the crude residue was taken up with boiling EtOH and was filtered. A yellowish solid was obtained which, after drying, yielded 60 g., m.p. 161°–163° C.

EXAMPLE 2

2,3-Dichloro-4-(4'-hydroxybenzoyl)phenoxyethanol

Dry DMF (40 ml.) was cooled in an ice bath to 10°–15° C. Sodium hydride (7.2 g., 0.15 mole) was then added. The suspended mixture was stirred for 10 minutes and acetaldoxime (11.8 g., 0.2 mole) was added portionwise. After stirring for another 10 minutes the compound from Example 1 (17.8 g., 0.05 mole) in 30 ml. dry DMF was added dropwise. When the addition was completed, the ice bath was removed and the reaction mixture was stirred at room temperature for 2½ hours. The mixture was poured into ice water and was filtered. The filtrate was acidified with concentrated HCl to obtain a precipitate. The crude solid was purified from aqueous ethanol to yield 11 g. (67%), m.p. 169°–170° C.

EXAMPLE 3

2,3-Dichloro-4-[(3'-chloroacetamidomethyl-4'-hydroxy)benzoyl]phenoxyethanol

The compound from Example 2 (6 g., 0.0183 mole) was added portionwise to stirred, concentrated $H_2SO_4$ (30 ml.) at room temperature for 20 minutes. With cooling to 10°–15° C., N-hydroxymethyl chloroacetamide (2.266 g., 0.0183 mole) was added in one portion. After the addition was completed, the dark mixture was stirred at 10°–15° C. for 2½ hours. It was poured into 150 g. ice and the resulting mixture was extracted with ethyl acetate a few times. The organic portion was washed with cold water, dried ($Na_2SO_4$) and filtered. The filtrate was evaporated under reduced pressure to give an amorphous solid. It was triturated with ether for 5 minutes and filtered to obtain 3.5 g. of crude product. This material was recrystallized from aqueous EtOH to give 2.4 g. (30%), m.p. 178°–180° C.

EXAMPLE 4

2,3-Dichloro-4-[(3'-aminomethyl-4'-hydroxy)benzoyl]-phenoxyethanol, hydrochloride A mixture of the compound from Example 3 (2.3 g., 0.0053 mole), 15 ml. concentrated HCl and 20 ml. ethanol was refluxed for 5½ hours. The mixture was evaporated under reduced pressure to almost dryness to obtain an amorphous solid. It was triturated with several ml. of ethanol and filtered to obtain 1.8 g. (83%) of pure product, m.p. 127°–130° C.

Analysis Calcd. for $C_{16}H_{15}Cl_2NO_4 \cdot HCl \cdot 1\frac{1}{2}H_2O$: C, 45.77; H, 4.53; N, 3.34 Found: C, 46.06; H, 4.27; N, 3.40

EXAMPLE 5

Ethyl 2,3-dichloro-4-(4'-hydroxybenzoyl)phenoxyacetate

An 85.38 g. (0.25 mole) portion of 2,3-dichloro-4-(4'-hydroxybenzoyl)phenoxyacetic acid, 34.5 g. (0.75 mole) of ethanol, and 100 ml. of ethylene dichloride, using 3.5 ml. of sulfuric acid as the catalyst was mixed and refluxed with stirring overnight according to the procedure of Clinton and Laskowski, J.A.C.S. 70 3135, 1948. The acid gradually went into solution. The reaction layer was cooled, separated and the organic layer washed successively with water, twice with $KHCO_3$ solution and finally with water. The dried ethylene dichloride was evaporated to dryness to give an oil which solidified to give 86 g. crude ester on trituration with pentane and filtering; m.p. 127°–9° (93% yield). This material was used without further purification in subsequent experiments.

EXAMPLE 6

Ethyl 2,3-dichloro-4-[(3'-chloro-4'-hydroxy)benzoyl]-phenoxyacetate

A mixture of 50 ml. ethylene dichloride and 9.2 g. (0.025 mole) of ethyl 2,3-dichloro-4-(4'-hydroxybenzoyl)phenoxyacetate was treated with 2.5 g. (0.03 mole) of $SO_2Cl_2$. The mixture was heated on a steam bath at reflux for 6 hours. The solvent was removed to give a white solid. This was collected with the aid of ether to give 8.5 g. of a solid; m.p. 135°–40°. Recrystallization with toluene with Darco gave 4.5 g. of the product; m.p. 152°–155°.

Analysis Calcd. for $C_{17}H_{13}Cl_3O_5$=403.65 C, 50.59; H, 3.24; Cl, 26.35 Found: C, 50.55; H, 3.12; Cl, 25.80

EXAMPLE 7

Ethyl 2,3-dichloro-4-[(3'-chloroacetamidomethyl-4'-hydroxy-5'-chloro)benzoyl]phenoxy acetate 2-Chloro-N-(hydroxymethyl)acetamide (2.59 g., 0.021 mole) was added, in small portions, to a stirred solution of 10.1 g. (0.02 mole) of ethyl 2,3-dichloro-4-(3'-chloro-4'-hydroxybenzoyl)phenoxyacetate in 35 ml. methanesulfonic acid at 40°–50°. After the addition, the mixture was stirred and heated in an oil bath at 95° for 3¾ hours. On cooling, the mixture was poured into ice water; the solid was filtered and washed with water. The crude dried product was dissolved in 500 ml. of ethanol and 3 ml. of concentrated $H_2SO_4$ and stirred overnight at room temperature. The ethanol was partly evaporated under reduced pressure and the residue distributed between methylene chloride and aqueous NaHCO₃. Evaporation of the methylene chloride gave the ethyl ester, which was used without further purification in the subsequent experiment. The compound had m.p. 137°–139°.

EXAMPLE 8

2-{2,3-Dichloro-4-[(3'-chloroacetamidomethyl-4'-hydroxy-5'-chloro)benzoyl]}phenoxyethanol A 10 g. sample of the compound from Example 7 was dissolved in 175 ml. of ethanol and 25 ml. of methylene chloride. With cooling in an ice bath NaBH₄ was added portionwise over a period of 20 minutes (5 portions of 1.75 g. every five minutes). The reaction mixture was then stirred at 0°–5° for 40 minutes and poured onto ice. After acidification to pH=5–6, the aqueous solution was extracted with methylene chloride. Evaporation of the organic extract gave a residue which was chromatographed on silica gel eluting with 0.5% MeOH in methylene chloride. There was obtained 5.9 g. of pure product; m.p. 165°–166°.

Analysis Calcd. for $C_{18}H_{15}Cl_4NO_5$: C, 46.28; H, 3.24; N, 3.00 Found: C, 45.12; H, 3.35; N, 3.08

EXAMPLE 9

2-[2,3-Dichloro-4-(3'-aminomethyl-4'-hydroxy-5'-chloro)benzoyl]phenoxyethanol, hydrochloride A mixture of 5.5 g. of the compound from Example 8 in 135 ml. of ethanol and 55 ml. of concentrated HCl was heated at reflux. After 4.5 hours, the mixture was cooled and evaporated to dryness. The residue was triturated with ether to give 4.12 of product; m.p. 234°–236°.

Analysis Calcd. for $C_{16}H_{15}Cl_4NO_4$: C, 44.99; H, 3.54; N, 3.28 Found: C, 45.09; H, 3.56; N, 3.23

EXAMPLE 10

2,3-Dichloro-4-[(3'-benzyloxycarboxamidomethyl-4'-hydroxy)benzoyl]phenoxyacetamide To a mixture of ethyl 2,3-dichloro-4-(3'-aminomethyl-4'-hydroxy)benzoylphenoxyacetate hydrochloride (22.8 g., 0.052 mole) and N-benzyloxycarbonyloxysuccinimide (13.5 g., 0.054 mole) in 225 ml. of acetonitrile was added 5.4 g. (0.054 mole) of potassium bicarbonate in 60 ml. of water at 0°–5°. The reaction mixture was allowed to warm to room temperature and stirred an additional 1.5 hours. The resulting two phase mixture was placed in a separatory funnel and the aqueous layer removed. The organic layer was evaporated under reduced pressure and the residue dissolved in methylene chloride. The methylene chloride solution was washed with aqueous sodium bicarbonate solution and dried over magnesium sulfate. Evaporation of the organic solvent furnished the N-carbobenzoxy derivative which was crystallized from ethyl acetate/hexane to give 22 g., m.p. 117°–119°. A 5 g. portion of the N-carbobenzyloxy compound was dissolved in absolute ethanol and anhydrous ammonia was passed into the solution for 2 hours. After standing overnight at room temperature, the ethanol was evaporated under reduced pressure. The solid residue was dissolved in methyl cellosolve (100 ml.) and the solution acidified with concentrated HCl. The acidic solution was then poured into 350 ml. of cold water and the carboxamide derivative filtered and dried. There was obtained 4.4 g. of pure product; m.p. 185°–186°.

EXAMPLE 11

2,3-Dichloro-4-[(3'-benzyloxycarboxamidomethyl-4'-hydroxy)benzoyl]phenoxyacetonitrile To a solution of 25 g. (0.0533 mole) of the compound from Example 10 dissolved in 145 ml. of tetrahydrofuran and 50 ml. of methylene chloride was added 17.25 ml. of pyridine. To the resulting mixture cooled in an ice bath was added 16.56 ml. (0.117 mole) of trifluoroacetic anhydride dropwise over a period of 40 minutes. The reaction was then stirred for 2.5 hours at room temperature and poured into brine solution. After acidification to pH=3 with aqueous HCl, the aqueous solution was extracted with methylene chloride. Evaporation of the methylene chloride gave a viscous liquid which furnished a crystalline solid upon trituration with hexane. Recrystallization from hexane/EtOAc gave 19 g. of pure nitrile; m.p. 155°–157°.

EXAMPLE 12

2,3-Dichloro-4-[(3'-aminomethyl-4'-hydroxy)benzoyl]-phenoxyethylamine dihydrochloride A 10 g. sample of the compound from Example 11 was dissolved in 200 ml. of methyl cellosolve and hydrogenated in a Par Apparatus over 1 g. of 5% Pd-C in the presence of aqueous hydrochloric acid (2.5 equivalents). The catalyst was filtered and the solvent was evaporated to give 9.0 g. of crude dihydrochloride salt after trituration with ether. This material was purified by conversion to the bis-t-BOC derivative followed by high pressure liquid chromatography (HPLC). The bis-t-BOC derivative was obtained by treating 9.09 g. (0.021 mole) of the diamine salt with 10.0 g. (0.046 mole) of di-tert-butyldicarbonate in 50 ml. of dimethylformamide containing 6.4 ml. of triethylamine. After 1 hour at room temperature, the reaction was poured into brine solution and extracted with methylene chloride. The organic extract was washed 3 times with brine and dried over MgSO₄. Evaporation of the CH₂Cl₂ furnished the bis-t-BOC compound. Purification using HPLC gave 5.9 g. of pure material. The t-BOC groups were removed by stirring the 6.9 g. of compound in 50 ml. of saturated ethanolic HCl. After 5 hours the precipitated salt was filtered and washed with ether to give 3.26 g. of pure product; m.p. 224°.

Analysis Calcd. for $C_{16}H_{18}Cl_4N_2O_3$: C, 44.89; H, 4.24; N, 6.54 Found: C, 44.63; H, 4.37; N, 6.40

Diuretic Screening of the compounds of this invention was conducted in normotensive rats using the following procedure.

Female rats (Sprague-Dawley), weighing 175–225 grams, are placed on a diet of sucrose and water overnight. DOCA (deoxycorticosterone acetate), is prepared as a 2.5% suspension in 0.2% hydroxypropyl methylcellulose. Each rat is administered 0.2 ml. subcutaneously of the DOCA suspension 2 hours prior to treatment with the test compound.

The suspension or solutions of test compounds are prepared daily. The compounds are suspended in 0.2% hydroxypropyl methylcellulose (vehicle) and administered orally (by gavage) in 2 ml./kg. of the rat's body weight. Immediately after dosing, each rat is loaded with an isotonic mixture of NaCl and KCl in the ratio of 40:60 equivalent to 3% of the rat's body weight.

The rats are placed in individual stainless steel metabolism cages. No food or water is allowed during the experiment. Urine is collected for a 4 hour period. The volume of urine is measured at 4 hours and an aliquot is taken for analysis of urine sodium and potassium concentrations. Sodium and potassium are measured using an Instrumentation Labs Digital Flame Photometer. The data are reported in: volume ml.; sodium and potassium—meq./l.

Standard screening procedures involves the testing of 2 doses of each compound using 2 rats per dose in a 2-stage screening system. The normal screening doses are 30 and 100 mg./kg. orally. Urinary excretions of sodium and potassium are expressed as meq./kg. of the rat's body weight.

TABLE I

| Compound | R | $R_1$ | Y | $ED_2$ |
|---|---|---|---|---|
| 1 | H | —OH | Cl | 0.5 |
| 2 | Cl | —OH | Cl | 19 |
| 3 | H | —$NH_2$ | Cl | 18 |

The natriuretic potency of the compounds listed is reported as $ED_2$. This is the oral dose necessary to produce an excretion in the 0–4 hour period after dosing, of 2 milliequivalents of Na+ per kilogram (meq./kg.) in the rat urine.

What is claimed is:

1. A compound of the formula

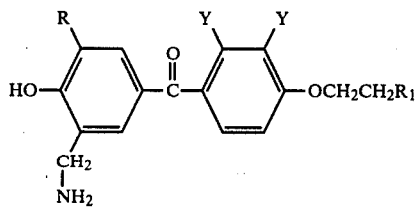

wherein R is hydrogen, loweralkyl, aminomethyl or halo, $R_1$ is hydroxy or NHX wherein X is hydrogen, loweralkyl, phenyl, acetyl, or benzyl, and Y may be the same or different and is hydrogen, loweralkyl, or halo, and pharmaceutically acceptable salts thereof.

2. A compound of claim 1 wherein R is hydrogen or halo, $R_1$ is hydroxy or amino, and Y is halo.

3. A compound of claim 2 wherein R is hydrogen, $R_1$ is hydroxy and Y is chloro.

4. A compound of claim 2 wherein R is chloro, $R_1$ is hydroxy and Y is chloro.

5. A compound of claim 2 wherein R is hydrogen, $R_1$ is amino, and Y is chloro.

6. A method of increasing the urinary excretion of a patient comprising administering to a patient in need of such treatment a therapeutically effective amount of a diuretic agent of the formula

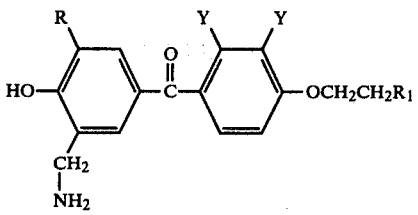

wherein R is hydrogen, loweralkyl, aminomethyl or halo, $R_1$ is hydroxy or NHX wherein X is hydrogen, loweralkyl, phenyl, acetyl, or benzyl, and Y may be the same or different and is hydrogen, loweralkyl or halo, and pharmaceutically acceptable salts thereof.

7. The method of claim 6 wherein R is hydrogen or halo, $R_1$ is hydroxy or amino, and Y is halo.

8. The method of claim 7 wherein R is hydrogen, $R_1$ is hydroxy and Y is chloro.

9. The method of claim 7 wherein R is chloro, $R_1$ is hydroxy and Y is chloro.

10. The method of claim 7 wherein R is hydrogen, $R_1$ is amino, and Y is chloro.

11. A pharmaceutical composition useful as a diuretic which comprises a therapeutically effective amount of a compound of the formula

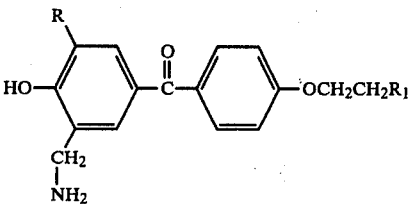

wherein R is hydrogen, loweralkyl, aminomethyl or halo, $R_1$ is hydroxy or NHX wherein X is hydrogen, loweralkyl, phenyl, acetyl, or benzyl, and Y may be the same or different and is hydrogen, loweralkyl, or halo, and pharmaceutically acceptable salts thereof, and a pharmaceutically acceptable carrier.

12. The composition of claim 11 wherein R is hydrogen or halo, $R_1$ is hydroxy or amino, and Y is halo.

13. The composition of claim 12 wherein R is hydrogen, $R_1$ is hydroxy and Y is chloro.

14. The composition of claim 12 wherein R is chloro, $R_1$ is hydroxy and Y is chloro.

15. The composition of claim 12 wherein R is hydrogen, $R_1$ is amino and Y is chloro.

* * * * *